US011291623B2

(12) United States Patent
Shin et al.

(10) Patent No.: US 11,291,623 B2
(45) Date of Patent: Apr. 5, 2022

(54) COSMETIC COMPOSITION COMPRISING, AS ACTIVE INGREDIENT, COMPOSITE SEAWATER EXTRACT OF BRUSSELS SPROUTS, LIMA BEANS, AND ARTICHOKES

(71) Applicant: AMOREPACIFIC CORPORATION, Seoul (KR)

(72) Inventors: Su Jeong Shin, Yongin-si (KR); Kil Sun Myoung, Yongin-si (KR); Bo Hyun Shin, Yongin-si (KR); Eun Soo Lee, Yongin-si (KR); Yu Jin Jin, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 14 days.

(21) Appl. No.: 16/767,789

(22) PCT Filed: Oct. 4, 2018

(86) PCT No.: PCT/KR2018/011738
§ 371 (c)(1),
(2) Date: May 28, 2020

(87) PCT Pub. No.: WO2019/107727
PCT Pub. Date: Jun. 6, 2019

(65) Prior Publication Data
US 2021/0212924 A1 Jul. 15, 2021

(30) Foreign Application Priority Data

Nov. 29, 2017 (KR) ........................ 10-2017-0161704

(51) Int. Cl.
*A61K 36/00* (2006.01)
*A61K 8/9789* (2017.01)
*A61K 8/96* (2006.01)
*A61Q 17/00* (2006.01)
*A61Q 19/00* (2006.01)

(52) U.S. Cl.
CPC ............ *A61K 8/9789* (2017.08); *A61K 8/965* (2013.01); *A61Q 17/00* (2013.01); *A61Q 19/007* (2013.01)

(58) Field of Classification Search
None
See application file for complete search history.

(56) References Cited

U.S. PATENT DOCUMENTS

| 5,322,839 A | 6/1994 | Voegeli et al. |
| 7,544,375 B1 | 6/2009 | Bellin et al. |

FOREIGN PATENT DOCUMENTS

| CN | 103961681 A | 8/2014 |
| JP | 2001-199868 A | 7/2001 |
| KR | 10-0271392 B1 | 11/2000 |
| KR | 10-2005-0111667 A | 11/2005 |
| KR | 10-2014-0090896 A | 7/2014 |
| KR | 10-2015-0007464 A | 1/2015 |
| KR | 10-2016-0123732 A | 10/2016 |
| KR | 10-2017-0065159 A | 6/2017 |

OTHER PUBLICATIONS

International Search Report of PCT/KR2018/011738 dated Jan. 14, 2019 [PCT/ISA/210].

*Primary Examiner* — Russell G Fiebig
(74) *Attorney, Agent, or Firm* — Sughrue Mion, PLLC

(57) ABSTRACT

The present disclosure relates to a cosmetic composition, and more specifically to a cosmetic composition for skin moisturization. The composition contains, as an active ingredient, a composite seawater extract obtained by mixing each of seawater extracts of Brussels sprouts, lima beans, and artichokes. The composite extract extracted from vegetables of Brussels sprouts, lima beans and artichokes by a natural method using seawater has excellent skin water loss-preventing and skin barrier-enhancing effects, and superior skin moisturizing ability. Therefore, the cosmetic composition containing the composite extract, as an active ingredient, can be advantageously used as a cosmetic material having excellent skin moisturizing ability.

7 Claims, 1 Drawing Sheet

[FIG. 1]
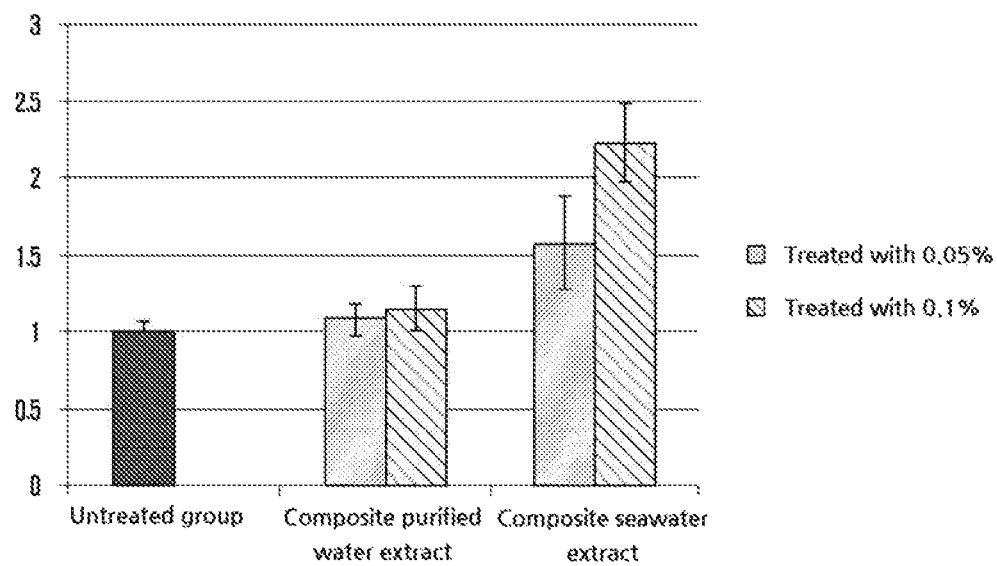
[FIG. 2]
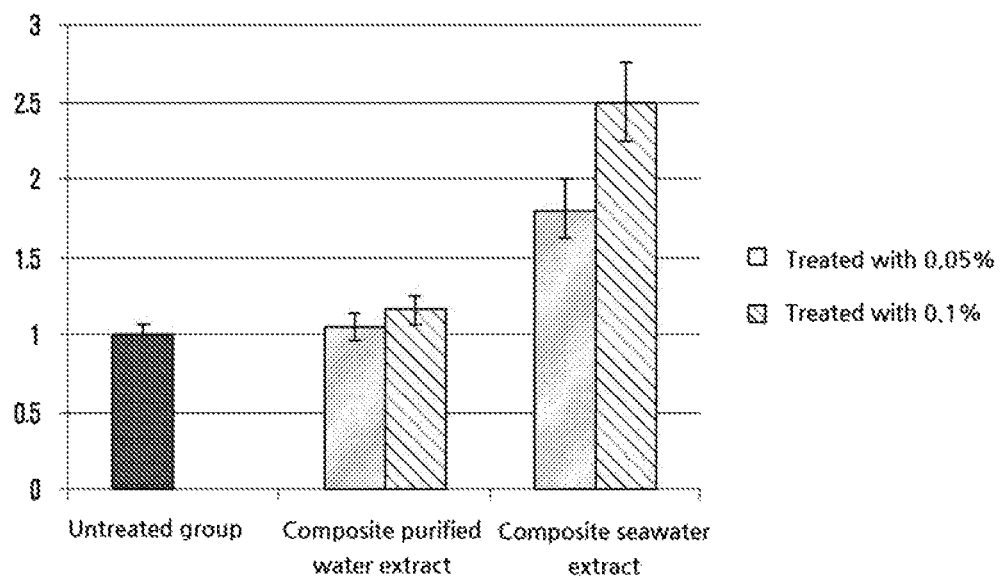

COSMETIC COMPOSITION COMPRISING, AS ACTIVE INGREDIENT, COMPOSITE SEAWATER EXTRACT OF BRUSSELS SPROUTS, LIMA BEANS, AND ARTICHOKES

CROSS REFERENCE TO RELATED APPLICATIONS

This application is a National Stage of International Application No. PCT/KR2018/011738, filed Oct. 4, 2018, claiming priority to Korean Patent Application No. 10-2017-0161704, filed Nov. 29, 2017, the contents of all of which are incorporated herein by reference in their entirety.

TECHNICAL FIELD

One aspect of the present disclosure relates to a cosmetic composition, and more specifically to a cosmetic composition for skin moisturization including, as an active ingredient, a composite seawater extract obtained by mixing each of seawater extracts of Brussels sprouts, lima beans and artichokes. Another aspect of the present disclosure relates to the use of a mixture of a seawater extract of Brussels sprouts, a seawater extract of lima beans, and a seawater extract of artichokes, as an active ingredient, in the preparation of a cosmetic composition, preferably a cosmetic composition for skin moisturization. Yet another aspect of the present disclosure relates to a method for maintaining the skin moisturizing ability of a subject and/or improving the moisturization state, including the step of locally applying a cosmetic composition containing, as an active ingredient, a composite seawater extract of Brussels sprouts, lima beans and artichokes to the skin of a subject.

BACKGROUND ART

Skin is largely divided into three layers: the epidermis, the dermis and the hypodermis, and plays a role in protecting the human body from physical and chemical stimulations from the external environment. Especially, the skin regulates that about 65-70% of water possessed by the human body is evaporated out of the body. Among them, the epidermis is sequentially divided into the stratum corneum, the stratum granulosum, the stratum spinosum and the stratum basale, and the stratum corneum of the epidermis contains about 10 to 20% of water, and prevents water inside the body from evaporating and blocks excessive penetration of materials from the outside by being located at the outermost layer of the human body (*J. Invest. Dermatol.* 80(*Suppl.*), 44-49. 1973). The water-soluble natural moisturizing factors (NMF) are present at high concentrations in the cells of the stratum corneum, and these factors not only function to provide flexibility to the skin, but also help to maintain water at suitable level (*J. Invest. Dermatol.* 54, 24-31, 1970). However, due to a variety of reasons, including changes in the environment or changes in life patterns, various stresses caused by social life and environmental pollution, frequent cleansing due to makeup and natural aging of the skin with aging, and the like, the water content of the stratum corneum decreases and thereby, the skin tends to become dry, the surface of which becomes rough, and the skin loses luster and may look dull. Thus, the importance of solving the problem associated with skin moisturization has been increasing.

Thus, various cosmetic raw ingredients having a skin moisturizing function are being developed. In the case of chemical raw materials, there are problems such as causing side effects including skin allergy or skin trouble. In the case of animal raw materials, the use of animal raw materials is rapidly decreasing due to a decrease in consumer preferences and the controversy of mad cow disease, and the like. Thus, environment-friendly raw materials such as plant-based raw materials have gained much interest.

PRIOR ART DOCUMENTS

Patent Documents (Patent Document 1) Korean Patent Application Publication No. 10-2014-0090896
(Patent Document 2) Korean Patent Application Publication No. 10-2005-0111667

DETAILED DESCRIPTION OF THE INVENTION

Technical Problem

It is one object of present disclosure to provide a cosmetic composition having excellent effects of enhancing the barrier function of the skin and improving skin moisturizing ability by promoting the expression of skin barrier-related genes and genes that prevent water release from the skin cells.

Technical Solution

In order to achieve the object above, one aspect of the present disclosure provides a cosmetic composition containing, as an active ingredient, a composite seawater extract of Brussels sprouts, lima beans and artichokes.

Another aspect of the present disclosure provides the use of a mixture of a seawater extract of Brussels sprouts, a seawater extract of lima beans, and a seawater extract of artichokes, as an active ingredient, in the preparation of a cosmetic composition, preferably a cosmetic composition for skin moisturization.

Yet another aspect of the present disclosure provides a method for maintaining the skin moisturizing ability of a subject and/or improving the moisturization state, including the step of locally applying a cosmetic composition containing, as an active ingredient, a composite seawater extract of Brussels sprouts, lima beans and artichokes to the skin of a subject.

Advantageous Effects

The composite extract extracted using vegetables of Brussels sprouts, lima beans and artichokes by a natural method using seawater according to the present disclosure has excellent skin water release-preventing and skin barrier-enhancing effects and superior skin moisturizing ability. Therefore, the cosmetic composition containing the composite extract as an active ingredient can be advantageously used as a cosmetic material having excellent skin moisturizing ability.

BRIEF DESCRIPTION OF THE DRAWINGS

FIG. 1 is a graph comparing the expression level of the ABCA12 gene according to Test Example 1.

FIG. 2 is a graph comparing the expression level of the occludin gene according to Test Example 2.

DETAILED DESCRIPTION OF THE EMBODIMENTS

Unless otherwise defined, all technical and scientific terms used herein have the same meaning as commonly understood by one of ordinary skill in the technical field to which the present disclosure belongs. In general, the nomenclatures used herein are those well-known and commonly used in the art.

Hereinafter, the cosmetic composition according to the present disclosure will be described in detail.

As used herein, the term "about" used to express the volume, time (duration), concentration, content, area, temperature, and the like means that there is a maximum tolerance of 10% in the corresponding numerical value or range.

The cosmetic composition according to one embodiment of the present disclosure contains, as an active ingredient, a composite seawater extract of Brussels sprouts, lima beans and artichokes.

Brussels sprouts used as an active ingredient in the cosmetic composition of the present disclosure is also referred to as *Brassica oleracea* L. var. *gemmifera Zenker*. Brussels sprouts are known to have superior storage period and significantly high contents of nutrients such as proteins, calcium, phosphorus, iron, vitamin A, vitamin C, and the like compared to common cabbage.

Lima beans used as an active ingredient in the cosmetic composition of the present disclosure are the oldest type of beans in South America and are native to Central and South America.

Lima beans, like other types of beans, are rich in protein and low in calories and in fat and thus can be used as foods that can give a feeling of satiety during weight control, and contains a high content of fiber, and thereby helps prevent lifestyle diseases such as arteriosclerosis and high blood pressure by lowering cholesterol level in the body as well as constipation. It also contains isoflavones, which is known to help prevent breast cancer.

Artichoke (*Cynara scolymus*), which is used as an active ingredient in the cosmetic composition of the present disclosure, is a perennial plant that looks like a thistle belonging to the Asteraceae family and is a plant that is characterized by a giant flower that resembles a thistle as a giant thistle. It is conveyed that it has been cultivated since the ancient Greek or Roman times and used as a food. Artichoke contains saccharides that act like insulin and thus is highly recognized for its medicinal purposes, and is known to have a cholesterol-lowering effect in the leaves and roots. When used as a tea, it helps to improve the diuretic action and the liver function. In addition, it shows effects in preventing lifestyle diseases such as potent antioxidant activity, protective function of hepatocytes, blood glucose control and the like, and in promoting digestion.

The composite seawater extract of Brussels sprouts, lima beans and artichokes according to the present disclosure may be prepared by obtaining each of seawater extracts of Brussels sprouts, lima beans and artichokes, and mixing them, or by mixing Brussels sprouts, lima beans and artichokes and extracting the mixture with seawater. It may preferably be a mixed extract prepared by obtaining each of seawater extracts of Brussels sprouts, lima beans and artichokes, and mixing them.

The Brussels sprouts, lima beans and artichokes may be extracted by a known extraction method for natural substances, and the solvent used for extraction may be seawater. The amount of seawater may vary depending on the amount of the seawater extract of Brussels sprouts, the seawater extract of lima beans, and the seawater extract of artichokes. For example, the seawater extract may be prepared by adding seawater 5 to 1000 times, preferably 5 to 100 times, and most preferably 10 to 30 times the weight of each of Brussels sprouts, lima beans and artichokes to Brussels sprouts, lima beans and artichokes, and immersing them therein.

In this case, the extraction temperature may be 5 to 60° C., preferably 12 to 30° C., more preferably 10 to 20° C., and extraction time is not particularly limited, but the extraction may be carried out, for example, for 1 to 24 hours, preferably 2 to 12 hours, more preferably 4 to 6 hours.

The composite seawater extract of Brussels sprouts, lima beans, and artichokes may be prepared by a known extraction method for natural substances as necessary. For example, it may be extracted by cold water extraction, hot water extraction, ultrasonic extraction, reflux extraction, and heat extraction, and it may be preferably extracted by hot water extraction or reflux extraction, and the extraction can be repeated 1 to 10 times, preferably 2 to 7 times.

The composite seawater extract of Brussels sprouts, lima beans and artichokes may be used as a liquid by filtration, and preferably, it may be used as a solid through a drying process such as spray drying or freeze drying. More preferably, it may be mixed with dextrin before carrying out spray drying or freeze drying and dried.

In the present disclosure, the composite seawater extract of Brussels sprouts, lima beans and artichokes may be prepared by mixing a seawater extract of Brussels sprouts, a seawater extract of lima beans, and a seawater extract of artichokes in a weight ratio of 1:1:3 to 50.

Further, in order to achieve the desired effects, the composite seawater extract of Brussels sprouts, lima beans and artichokes may be contained in an amount of 0.001 to 40% by weight, preferably 0.01 to 30% by weight, more preferably 0.1 to 10% by weight based on the total weight of the composition.

In the present disclosure, considering the formulation stability and the limited content of use based on the regulations concerning the safety of cosmetics, when the total weight of the composite seawater extract of Brussels sprouts, lima beans and artichokes is less than 0.001% by weight, the desired efficacy of enhancing the barrier function of the skin and/or improving the moisturizing ability of the skin may be not exhibited as a cosmetic material. Further, when the total weight exceeds 40% by weight, the composite seawater extract may not be sufficiently dissolved in the cosmetic formulation, so that it may not be stably mixed with other ingredients of the cosmetic formulation, and in addition, there may be problems in terms of safety such as excessive skin irritation when applied to the skin.

Meanwhile, in the present disclosure, the seawater may be common seawater, deep ocean water, lava seawater, or the like, but is not limited thereto. Preferably, it may be seawater withdrawn from 30 to 150 m underground (based on average sea level), preferably 44.35 m, 86.35 m, or 126.35 m by excavating 100 to 200 m underground, preferably 150 min Handong-ri, Gujwa-eup, North Jeju-gun, eastern Jeju-do.

In addition, the density of the seawater may vary depending on the temperature, pressure and salinity of the seawater, but is usually 1000 to 2000 g/L, preferably 1002 to 1100 g/L, more preferably 1005 to 1045 g/L. Such seawater may be those desalinated using a conventionally known desalination method, such as flash vaporization method, seawater freezing method, reverse osmosis, ion exchange resin method, electrodialysis method (ED), or using a commercially available electrodialyzer or desalter after removing impurities such as microorganisms of seawater collected by a sterile filter, preferably a 0.2 μm filter, and preferably, it may be those desalinated by an electrodialysis method which can control the mineral concentration and hardness of the desalinated seawater by varying its electrical conductivity value. For example, when using the electrodialysis method, the desalinated seawater may be prepared through a desalination process which removes monovalent cations and divalent anions by adjusting the electrical conductivity values to 8 mS/cm, 10 mS/cm, 12 mS/cm, 15 mS/cm or the like.

The cosmetic composition of the present disclosure may further include ingredients commonly used in cosmetic compositions in addition to the active ingredients. For example, it may include a conventionally adjuvant such as fatty materials, organic solvents, solubilizer, thickeners, gelling agents, softeners, antioxidants, suspending agents, stabilizers, foaming agents, aromatics, surfactants, water, ionic or non-ionic emulsifiers, fillers, sequestering agents, chelators, preservatives, vitamins, blockers, humectants, essential oils, dyes, pigments, perfumes, hydrophilic or lipophilic activating agents, and a carrier. In addition, these adjuvants or carriers are introduced in amounts commonly used in the cosmetic or dermatological field.

The cosmetic composition according to the present disclosure may be prepared in a conventionally prepared formulation in the art. For example, it may be formulated into solution, suspension, emulsion, paste, gel, cream, lotion, powder, soap, surfactant-containing cleansing, oil, powder foundation, emulsion foundation, wax foundation, pack, massage cream, spray, and the like, but is not limited thereto. More particularly, the cosmetic composition may be prepared into a formulation of softening cosmetic water, nourishing cosmetic water, nourishing cream, massage cream, essence, eye cream, cleansing cream, cleansing foam, cleansing water, facial pack, spray or powder.

The present disclosure relates to the use of a mixture of a seawater extract of Brussels sprouts, a seawater extract of lima beans, and a seawater extract of artichokes, as an active ingredient, in the preparation of a cosmetic composition, preferably a cosmetic composition for skin moisturization.

The present disclosure relates to a method for maintaining the skin moisturizing ability of a subject and/or improving the moisturization state, including the step of locally applying a cosmetic composition containing, as an active ingredient, a composite seawater extract of Brussels sprouts, lima beans, and artichokes to the skin of a subject.

MODE FOR CARRYING OUT THE INVENTION

Hereinafter, the present disclosure will be described in more detail by way of Example and Test Examples. However, these Examples and Test Examples are given for illustrative purposes only to help understanding of the present disclosure, and the scope of the present disclosure is not limited by these examples. Further, modifications, substitutions, and insertions commonly known in the art may be performed, these are also included in the scope of the present disclosure.

Reference Example

Brussels sprouts, lima beans, and artichoke leaves used in the following experiments were obtained from retailers, and seawater was supplied from Durae Corporation.

Meanwhile, in order to compare the components of seawater and freshwater, the seawater collected at 86.35 m underground (based on average sea level) and other seawater collected at 44.35 m underground and 126.35 m underground were subjected to component analysis by the Korea Testing and Research Institute. The mineral contents (unit: ppm) of seawater obtained in Jeju at different sea levels are shown in Table 1 below.

TABLE 1

| Test Item | Seawater at 44.35 m | Seawater at 86.35 m | Seawater at 126.35 m | Fresh water at 1 m |
|---|---|---|---|---|
| Na | 11400 | 11400 | 10700 | 146 |
| Mg | 1510 | 1520 | 1390 | 0.49 |
| Ca | 460 | 490 | 431 | 9.20 |
| K | 643 | 540 | 621 | 38.5 |
| Cu | 0.00157 | 0.00113 | 0.00080 | 0.00069 |
| Co | — | — | — | — |
| Sn | — | — | — | — |
| Mo | 0.011 | 0.012 | 0.011 | 0.0014 |
| V | 3.28 | 3.53 | 0.01 | 0.013 |
| Ge | 0.0032 | 0.003 | 0.0025 | 0.00019 |
| Br | — | — | — | — |
| Sr | 1.18 | 1.31 | 1.30 | 0.05 |
| Ti | — | — | — | — |
| Ni | — | — | — | — |
| Si ($SiO_2$) | 7.23 | 6.19 | 1.21 | 1.21 |
| Zn | 0.0045 | 0.0039 | 0.0019 | 0.001 |
| Fe | 0.21 | 0.26 | 0.04 | 0.082 |
| Mn | 19.51 | 20.7 | 18.9 | 0.01 |
| Cl | 16629 | 18500 | 19900 | 262 |
| B | 3.35 | 3.73 | 0.15 | 0.15 |
| Li | 0.37 | 0.41 | 0.09 | 0.09 |
| Ba | 0.032 | 0.019 | 0.015 | 0.015 |
| Pb | 0.004 | 0.0013 | 0.00065 | 0.00091 |
| F | — | — | — | — |
| As | 0.01 | — | — | — |
| Se | 0.00005 | 0.00124 | 0.00086 | 0.000049 |
| Hg | — | — | — | — |
| CN | — | — | — | — |
| Cr | — | — | — | — |
| Cd | — | — | — | — |
| Al | 0.63 | 0.49 | 0.47 | 0.14 |

Example 1: Preparation of Composite Seawater Extract of Brussels Sprouts, Lima Beans and Artichoke 20 g of Brussels sprouts, 20 g of lima bean seeds and 200 g of artichoke leaves were respectively pulverized using a pulverizing device, and about 25-fold weight of seawater was added thereto based on the weight of each pulverized product of Brussels sprouts, lima beans, and artichoke leaves, and the products were immersed therein at about 15° C. for about 5 hours, and then filtered to obtain each extract. The each of seawater extracts of Brussels sprouts, lima beans and artichoke leaves were mixed to prepare a composite seawater extract of Brussels sprouts, lima beans and artichoke.

Comparative Example 1: Preparation of Composite Purified Water Extract of Brussels Sprouts, Lima Beans and Artichoke A composite purified water extract of Brussels sprouts, lima beans and artichoke was prepared in the same manner as in Example 1, except that purified water was used as an extraction solvent.

Test Example 1: Effect of Promoting Expression of ABCA12 Gene

The ABCA12 gene is a skin barrier-related gene, and is known to contribute to intercellular lipid formation by participating in lipid migration from the cytosol of keratinocytes to lamellar granules. Therefore, in order to confirm the effect of promoting the expression of the ABCA12 gene of the composite seawater extract of Brussels sprouts, lima beans and artichokes according to the present disclosure, an experiment was conducted as follows.

Human epidermal keratinocytes (HEKn, Lonza) were seeded into a 6-well plate medium (KBM-gold, Lonza) at a concentration of $2 \times 10^5$ cells/well and cultured for 24 hours under conditions of 37° C. and 5% $CO_2$. Here, the composite seawater extract of Example 1 was treated at 0.05% and 0.1% based on the volume, and further cultured for 24 hours. The further cultured keratinocytes were lysed with TRIzol (Invitrogen) to isolate RNA, and the isolated RNA was purified once more with an RNA kit (QIAGEN RNeasy kit, QIAGEN, Valencia, Calif.), and then the quality of RNA was examined using an bioanalyzer 2100 (Agilent 200 BioAnalyzer, Agilent Technologies, Santa Clara, Calif., USA). Thereafter, cDNA was synthesized using a Superscript Reverse Transcriptase (RT) kit, (Invitrogen, Carlsbad, Calif.). In order to confirm the expression level of the ABCA12 gene, real time PCR was performed using a probe (TaqMan™ fluorogenic probe, Hs00292421_m1) to observe the expression pattern of the ABCA12 gene. Here, for the analysis of the relative expression pattern for each sample, corrections were made based on the mRNA expression level of RPL13A (Ribosomal Protein L13a). The results are shown in FIG. 1. As a control group, the composite purified water extract of Comparative Example 1 was treated at 0.05% and 0.1% based on the volume to be used, instead of the untreated group and the composite seawater extract of Example 1. The y-axis value in FIG. 1 represents the relative gene expression level when the gene expression level of the untreated group was 1.

As shown in FIG. 1, it was confirmed that the composite seawater extract of Brussels sprouts, lima beans and artichokes according to the present disclosure greatly promoted the expression of the ABCA12 gene, which is a skin barrier-related gene, and it showed a remarkably excellent effect when treated at the same concentration as the composite purified water extract of Brussels sprouts, lima beans and artichokes.

Therefore, it was confirmed that the composite seawater extract of Brussels sprouts, lima beans and artichokes according to the present disclosure greatly promoted the gene expression of ABCA12, thereby providing excellent skin barrier-enhancing and skin moisturizing effects.

Test Example 2: Effect of Promoting Expression of mRNA of Occludin

Occludin, a cell membrane protein, is specifically expressed in tight junctions that play an important role in maintaining and strengthening the barrier function of the skin. When the expression of the occluded protein is inhibited, transepidermal water loss (TEWL) increases significantly, and thus, it can be suggested that occludin is highly related to water loss (Bazzoni et al., *J Cell Biol.*, 156(6): 947-9. 2002; Furuse et al., *J Cell Biol.*, 156(6):1099-111, 2002; Nakajima et al., *J Pharmacol Exp Ther.*, 354(3):440-7, 2015; Volksdorf et al., *Am J Pathol.*, 187(6):1301-1312, 2017; Papakonstantinou et al., *Dermatoendocrinol.*, 4(3): 253-8, 2012).

Therefore, in order to investigate the effect of promoting the expression of the occludin coding gene (mRNA) of the composite seawater extract Brussels sprouts, lima beans and artichokes according to the present disclosure, an experiment was conducted as follows.

Human epidermal keratinocytes (HEKn, Lonza) were seeded into a 6-well plate medium (KBM-gold, Lonza) at a concentration of $2 \times 10^5$ cells/well and cultured for 24 hours under conditions of 37° C. and 5% $CO_2$. Here, the composite seawater extract of Example 1 was treated at 0.05% and 0.1% based on the volume, and further cultured for 24 hours. The further cultured keratinocytes were lysed with TRIzol (Invitrogen) to isolate RNA, and the isolated RNA was purified once more with an RNA kit (QIAGEN RNeasy kit, QIAGEN, Valencia, Calif.), and then the quality of RNA was examined using an bioanalyzer 2100 (Agilent 200 BioAnalyzer, Agilent Technologies, Santa Clara, Calif., USA). Thereafter, cDNA was synthesized using a Superscript Reverse Transcriptase (RT) kit, (Invitrogen, Carlsbad, Calif.). In order to confirm the expression level of the occludin gene, real time PCR was performed using a probe (TaqMan™ fluorogenic probe, Hs00170162_m1) to observe the mRNA expression level of the occludin gene. Here, for the analysis of the relative expression pattern for each sample, corrections were made based on the mRNA expression level of RPL13A (Ribosomal Protein L13a). The results are shown in FIG. 2. As a control group, the composite purified water extract of Comparative Example 1 was treated at 0.05% and 0.1% based on the volume to be used, instead of the untreated group and the composite seawater extract of Example 1. The y-axis value in FIG. 2 represents the relative gene expression level when the gene expression level of the untreated group was 1.

As shown in FIG. 2, it was confirmed that the composite seawater extract of Brussels sprouts, lima beans and artichokes according to the present disclosure greatly promoted the mRNA expression of occludin, which is a tight-junction-related protein, and it showed a remarkably excellent effect when treated at the same concentration as the composite purified water extract of Brussels sprouts, lima beans and artichokes.

Therefore, it was confirmed that the composite seawater extract of Brussels sprouts, lima beans and artichokes according to the present disclosure greatly promoted the mRNA expression of occludin, thereby effectively preventing water release in the keratinocytes, and thus provides an excellent skin moisturizing effect.

The cosmetic composition for skin moisturization containing, as an active ingredient, the composite seawater extract of Brussels sprouts, lima beans and artichokes according to the present disclosure can be prepared into various formulations (cosmetics and the like), and can be controlled to a suitable content ratio in consideration of the functionality, cost, and other conditions of the product to be implemented.

Formulation Example 1: Preparation of Ointment

An ointment including the composite seawater extract of Brussels sprouts, lima beans and artichokes according to the present disclosure was prepared by mixing the ingredients shown in Table 2 below including the oil-phase ingredients and aqueous-phase ingredients.

TABLE 2

| Mixing Ingredients | Content(wt %) |
| --- | --- |
| Purified water | balance |
| Composite seawater extract of Brussels sprouts, lima beans, and artichokes | 10.0 |

TABLE 2-continued

| Mixing Ingredients | Content(wt %) |
| --- | --- |
| Caprylic/Capric triglyceride | 10.0 |
| Liquid paraffin | 10.0 |
| Sorbitan sesquioleate | 6.0 |
| Octyldodeceth-25 | 9.0 |
| Cetyl ethyl hexanoate | 10.0 |
| Squalane | 1.0 |
| Salicylic acid | 1.0 |
| Glycerin | 15.0 |
| Sorbitol | 10.0 |

Formulation Example 2: Preparation of Nourishing Cosmetic Water (Milk Lotion)

A nourishing cosmetic water including the composite seawater extract of Brussels sprouts, lima beans and artichokes according to the present disclosure was prepared by mixing the ingredients shown in Table 3 below including the oil-phase ingredients and aqueous-phase ingredients.

TABLE 3

| Mixing Ingredients | Content(wt %) |
| --- | --- |
| Purified water | balance |
| Composite seawater extract of Brussels sprouts, lima beans, and artichokes | 0.1 |
| Beewax | 4.0 |
| Polysorbate 60 | 1.5 |
| Sorbitan sesquioleate | 1.5 |
| Liquid paraffin | 0.5 |
| Montana 202 (Manufacturer: Seppic) | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservatives, pigments, perfumes | q.s. |

Formulation Example 3: Preparation of Massage Cream

A massage cream including the composite seawater extract of Brussels sprouts, lima beans, and artichokes according to the present disclosure was prepared by mixing the ingredients shown in Table 4 below including the oil-phase ingredients and aqueous-phase ingredients.

TABLE 4

| Mixing Ingredients | Content(wt %) |
| --- | --- |
| Purified water | balance |
| Composite seawater extract of Brussels sprouts, lima beans, and artichokes | 0.1 |
| Beewax | 10.0 |
| Polysorbate 60 | 1.5 |
| PEG-60 Hydrogenated castor oil | 2.0 |
| Sorbitan sesquioleate | 0.8 |
| Liquid paraffin | 40.0 |
| Squalane | 5.0 |
| Montana 202 (Manufacturer: Seppic) | 4.0 |
| Glycerin | 5.0 |
| Butylene glycol | 3.0 |
| Propylene glycol | 3.0 |

TABLE 4-continued

| Mixing Ingredients | Content(wt %) |
| --- | --- |
| Triethanolamine | 0.2 |
| Preservatives, pigments, perfumes | q.s. |

Formulation Example 4: Preparation of Pack

A pack including the composite seawater extract of Brussels sprouts, lima beans, and artichokes according to the present disclosure was prepared by mixing the components shown in Table 5 below including the oil-phase ingredients and aqueous-phase ingredients.

TABLE 5

| Mixing Ingredients | Content(wt %) |
| --- | --- |
| Purified water | balance |
| Composite seawater extract of Brussels sprouts, lima beans, and artichokes | 0.1 |
| Polyvinyl alcohol | 13.0 |
| Sodium carboxymethylcellulose | 0.2 |
| Glycerin | 5.0 |
| Allantoin | 0.1 |
| Ethanol | 6.0 |
| PEG-12 nonylphenyl ether | 0.3 |
| Polysorbate 60 | 0.3 |
| Preservatives, pigments, perfumes | q.s. |

Although specific parts of the present disclosure have been described in detail, it will be apparent to those skilled in the art that these specific descriptions are merely a preferred embodiment and that the scope of the present disclosure is not limited thereto. Therefore, the substantial scope of the present disclosure will be defined by the accompanying claims and their equivalents.

The invention claimed is:

1. A method for maintaining skin moisturizing ability and/or improving moisturization state of skin of a subject, comprising the step of topically applying an effective amount of a cosmetic composition comprising, as an active ingredient, a composite seawater extract of Brussels sprouts, lima beans, and artichokes to the skin of the subject, wherein the composite seawater extract is obtained by mixing a seawater extract of Brussels sprouts, a seawater extract of lima beans, and a seawater extract of artichokes in a weight ratio of 1:1:3 to 50.

2. The method of claim 1, wherein the weight ratio of the seawater extract of Brussels sprouts, the seawater extract of lima beans, and the seawater extract of artichokes is 1:1:10.

3. The method of claim 1, wherein the composite seawater extract of Brussels sprouts, lima beans, and artichokes is contained in an amount of 0.001 to 40% by weight based on the total weight of the composition.

4. The method of claim 1, wherein the step of topically applying an effective amount of the cosmetic composition increases the expression level of ABCA12 gene of skin cells.

5. The method of claim 1, wherein the step of topically applying an effective amount of the cosmetic composition increases the expression level of a gene encoding occludin of skin cells.

6. The method of claim 1, wherein the step of topically applying an effective amount of the cosmetic composition enhances the barrier function of the skin.

7. The method of claim 1, wherein the step of topically applying an effective amount of the cosmetic composition improves skin moisturizing ability.

\* \* \* \* \*